United States Patent [19]
Glenn et al.

[11] Patent Number: 6,066,097
[45] Date of Patent: May 23, 2000

[54] TWO DIMENSIONAL ULTRASONIC SCANNING SYSTEM AND METHOD

[75] Inventors: William E. Glenn, Ft. Lauderdale, Fla.; Petko D. Dinev, Plainsboro, N.J.

[73] Assignee: Florida Atlantic University, Boca Raton, Fla.

[21] Appl. No.: 08/955,759

[22] Filed: Oct. 22, 1997

Related U.S. Application Data

[60] Provisional application No. 60/029,754, Oct. 22, 1996.

[51] Int. Cl.$^7$ .................................................. A61B 8/00
[52] U.S. Cl. .......................................................... 600/443
[58] Field of Search .................................. 600/437, 441, 600/442, 443, 447, 455–456

[56] References Cited

U.S. PATENT DOCUMENTS

| | | | |
|---|---|---|---|
| 5,233,993 | 8/1993 | Kawano | 600/443 |
| 5,285,788 | 2/1994 | Arenson et al. | 600/443 |
| 5,355,887 | 10/1994 | Iizulio et al. | 600/443 |
| 5,533,510 | 7/1996 | Koch, III et al. | 600/443 |

OTHER PUBLICATIONS

H. Fernandez and W. McKinney, 1971, Effect Of Auditory Stimulation On The Pulsatile Echo Blood Pressure And Electroencephalogram, Ultrasonics, pp. 138–141.

W. Hedrick, D. Hykes and Dale Starhman, 1995, Ultrasound Physics And Instrumentation, III ed., Mosby, St. L., pp. 88–123.

Pappalardo, M., 1981 Hybrid Linear And Matrix Acoustic Arrays, Ultrasonics, #3, pp. 81–86.

Whittingham, T., 1976, A Hand–Held Electronically Switched Array For Rapid Ultrasonic Scanning, Ultrasonics, #1, pp. 29–33.

P.D. Dinev and W.E. Glenn, A Two–Dimensional Ultrasonic Real Time Color Brain Scanner, Presented at International Neurosonology Conference, Winston Salem, NC, Aug., 1997.

P.D. Dinev and W.E. Glenn, Digitally Controlled Time Gain Compensation For Ultrasonic Scanners, Measur. Sci. Technol., 8, 1997.

E. Spudis et al., Pulsatile Echoencephalography, Neurology, vol. 19, Jul., 1969, pp. 667–673.

*Primary Examiner*—Francis J. Jaworski
*Attorney, Agent, or Firm*—Martin Novack

[57] ABSTRACT

An apparatus and method for producing an image of the brain by ultrasonic scanning, wherein brain metabolism is measured and displayed by monitoring amplitudes of localized changes of intracranial interfaces uses a flexible array applied to the scalp overlying the skull to produce a superposed grey scale image representing static structures and a color-coded pattern representing motion information.

9 Claims, 6 Drawing Sheets ered in the history of ultrasound for medical diagnostics, existing brain imaging techniques are non-ultrasonic in their nature. The most popular brain imaging techniques are Magnetic Resonance Imaging (MRI), and Position Emission Tomography (PET). The equipments providing such imaging are extremely expensive. Furthermore, PET requires chemical radioactive tracers, and MRI works with a strong magnetic field. Both techniques need a long integration time for metabolic activity or structure measurements (e.g. about 45 min. for PET, and 2 min. for MRI), so they are incapable of showing real time live pictures of the human brain.

TWO DIMENSIONAL ULTRASONIC SCANNING SYSTEM AND METHOD

RELATED APPLICATION

This application claims priority from U.S. Provisional Patent Application No. 60/029,754, filed Oct. 22, 1996, and said Provisional Patent Application is incorporated herein by reference.

FIELD OF THE INVENTION

This invention relates to ultrasonic imaging and, more particularly, to an ultrasonic scanning apparatus and method that can be used, inter alia, for obtaining images of the brain.

BACKGROUND OF THE INVENTION

The brain is an inaccessible organ that cannot be examined by visual, palpatory or auscultatory methods currently used in clinical medicine. Although the suggestion of brain imaging was made early in the history of ultrasound for medical diagnostics, existing brain imaging techniques are non-ultrasonic in their nature. The most popular brain imaging techniques are Magnetic Resonance Imaging (MRI), and Position Emission Tomography (PET). The equipments providing such imaging are extremely expensive. Furthermore, PET requires chemical radioactive tracers, and MRI works with a strong magnetic field. Both techniques need a long integration time for metabolic activity or structure measurements (e.g. about 45 min. for PET, and 2 min. for MRI), so they are incapable of showing real time live pictures of the human brain.

There are several real time, two-dimensional color ultrasonic scanning techniques currently used in clinical diagnosis. The most popular are Color M-Mode Scanning and Color Doppler. However, they are not applicable for brain imaging, and also suffer some disadvantages.

The image in Color M-mode Scan is interpreted by pattern recognition, but it does not correlate with the usual two dimensional structure anatomy as depicted in real time imaging. The detected motion in the lateral direction is not portrayed because of the limited field of view. Furthermore, this scanning is based on two-dimensional extrapolation of geometric shapes based on one dimensional measurement, which introduces an error. This scanner is mainly used in echocardiology.

The major disadvantages of duplex scanning in Color Doppler are related to the fact that the flow is not evaluated simultaneously throughout the field of view but rather is sampled at a particular location as selected by the sonographer. To establish the region flow pattern, an FFT analysis must be performed at multiple sites throughout the vessel, which requires precise positioning of the sampling volume; color coding is based on the average, rather than the peak Doppler shift; progressing across the field of view, a vessel with constant flow is depicted with different colors and so on. The highest priority for such a scanner is the observation of arterial and venous flow. Furthermore, such techniques are based on a velocity detection, so they are not able to measure small amplitude variations, and cannot provide imaging through the skull.

It is among the objects of the present invention to provide improvement over prior art ultrasonic techniques for imaging the body, and which can be used for practical imaging and diagnosis of the brain.

SUMMARY OF THE INVENTION

The disclosed new type of two-dimensional, real time, color ultrasonic scanner is able to measure and display brain metabolism by monitoring amplitudes of localized changes of intracranial interfaces. A real time image is obtained with a flexible array of transducers which eliminates the strong reflection from the skull due to a shape mismatch, and reduces the topological mislocations in the image. The image is generated by a superposition of a gray scale image representing static structures, and a color coded pattern representing motion information. The pulsations observed in certain parts of the brain are depicted by image subtraction. In this way, only the regions where these pulsations occur can be observed. All other echoes will be canceled during subtraction, since they represent static structures. The motion detection, based on image subtraction, gives the scanner the capability to detect multidirectional motion of the intracranial interfaces, and to display the amplitude of the motion in real time. A digitally controlled time-gain compensation allows imaging of preselected brain areas. Monitoring the image synchronously with the heart beat and an external stimulus presence can give clinicians the opportunity of a real time visualization of detailed cross-sectional anatomy of portions of the human brain, permitting direct observation, mapping the structure and function in a normal human brain, and studying the pathophysiology of brain abnormalities by demonstrating structural, metabolic, and neurochemical abnormalities.

The scanner hereof can also be applied in other areas of medical diagnosis beyond neurology, for example as echocardiology or gynecology. Although the scanner is designed primarily for medical imaging, some of the features hereof can also be applied to sonar, nondestructive testing (NDT) of materials, or precision motion sensing.

In accordance with a form of the invention there is disclosed an apparatus for producing an image of a body, comprising: transmitter means for producing energizing signals; transducer means coupled with the transmitter means for producing ultrasonic energy for transmission into the body and receiving ultrasonic energy reflected from the body; receiver means coupled with the transducer means for producing receiver signals; storage means for storing the receiver signals; difference means responsive to the receiver signals and an output of the storage means for producing motion signals as a function of the difference between the receiver signals and the storage means output; and means for displaying the motion signals.

In a preferred embodiment of this form of the invention, the means for displaying the motion signals comprises means for quantifying the amplitude of motion represented by the motion signals to produce motion amplitude signals, and means for displaying the motion amplitude signals. In this embodiment, the means for displaying the motion amplitude signals comprises means for color coding the motion amplitude signals with different colors for different motion amplitudes, and for displaying the coded colors.

In accordance with a further form of the invention there is provided a transducer array for use in an ultrasonic scanner for imaging a brain in a skull. The transducer array comprises: a flexible substrate that can conform to the shape of the skull; an array of transducers mounted on the substrate; a backing block mounted on the back of each transducer of the array; and means for coupling electric signals to and from each transducer of the array.

In a preferred embodiment of this form of the invention, the substrate is a plastic substrate and the array is a linear array of piezoelectric transducers individually mounted on the substrate. The backing blocks are formed of material having an acoustic impedance matched to that of the transducer material. Also, the substrate has an acoustic impedance that is between the acoustic impedance of the transducers and the acoustic impedance of the skull skin layer.

Further features and advantages of the invention will become more readily apparent from the following detailed description when taken in conjunction with the accompanying drawings.

DETAILED DESCRIPTION

Figure 1:
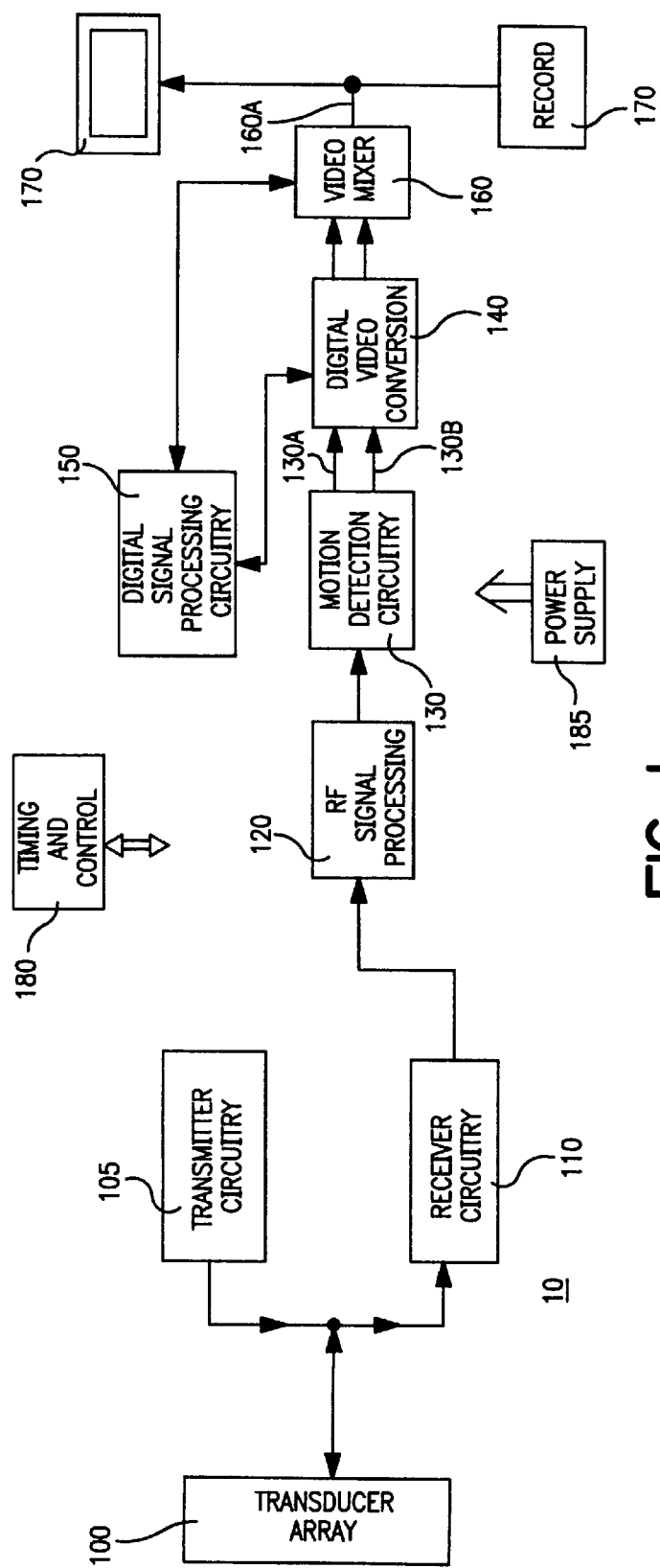
FIG. 1 is a block diagram of an apparatus in accordance with an embodiment of the invention and which can be used in practicing an embodiment of the method of the invention.

Referring to FIG. 1, there is shown a block diagram of an ultrasonic imaging apparatus 10 in accordance with an embodiment of the invention and which can be used to practice an embodiment of the method of the invention. [See also P. D. Dinev and W. E. Glenn, "A Two-Dimensional Real Time Color Brain Scanner", Presented at International Neurosonology Conference, Winston Salem, N.C., August, 1997, which is incorporated herein by reference.] The illustrated imaging apparatus includes a transducer array 100 that is coupled with both transmitter circuitry 105 and receiver circuitry 110. In the present embodiment, the transmitter is a radio frequency (RF) transmitter that generates a series of short high voltage pulses with a duration of about 200 nanoseconds (ns) and a leading edge of 10 ns, for energizing to the transducer array where the ultrasonic pulses are produced and transmitted. The RF receiver amplifies the return echo signals produced at the transducer array. The receiver circuit preferably has relatively high gain-bandwidth product, low noise, low phase distortion, and fast recovery characteristics, and has a gain in this embodiment of 60 dB in order to compensate for the relatively high attenuation at the skull. The output of RF receiver 110 is coupled to RF signal processing circuitry 120 which, in the present embodiment, compresses the 120 dB dynamic range of the received echo signal to an adequate dynamic range of about 40 dB, using digitally controlled time-gain compensation and logarithmic amplification. [Reference can be made, for example, to P. D. Dinev and W. E. Glenn, "Digitally Controlled Time Gain Compensation For Ultrasonic Scanners", Measur. Sci. Technol., 8, 1997, incorporated herein by reference.] The output of block 120 is coupled to a multidirectional motion detection circuit 130, which is described in further detail in conjunction with the diagram of FIG. 6. Briefly, in an embodiment hereof, the circuit 130 detects interface motion with a resolution of 10 $\mu$m by means of image subtraction. Using this technique, the echo-representative signals are transformed into spatially aligned signals; namely, a static signal 130A and a motion signal 130B. These signals are coupled to a digital video conversion circuit 140 which converts the incoming line rate to a standard (NTSC) 63 $\mu$s television line rate. In the preferred embodiment, the conversion is performed on the motion and the static signals simultaneously. The block 150 represents the digital signal processing circuitry that generates the control signals for the conversion and the color palette for the color coding of the motion signal. The block 160 receives and superimposes the static and color motion signals and provides an output which, in the present embodiment, is in NTSC format. The output signal 160A can be displayed, such as by color monitor 170 and/or stored, such as by video storage means 175, which may be, for example, a video cassette recorder or video disk storage. Circuitry 180 provides timing and control for the system, and power supply 185 provides the necessary power. In the present embodiment, the timing signals are derived from the same basic clock. Generation of the composite video signal as the system output requires an external clock frequency of 3.58 MHz for the color subcarrier. The system clock is established to be an eight multiple of the color subcarrier; i.e. 28.6363 MHz, and all timing signals are derived from this clock.

Figure 2:
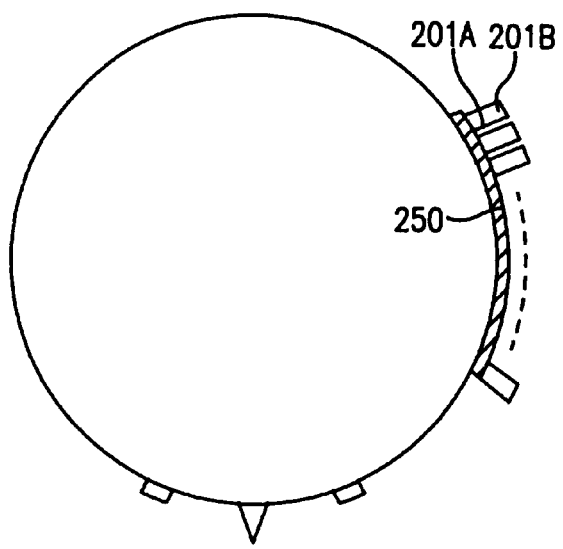
FIG. 2 illustrates a transducer array for brain scanning, mounted on a skull, in accordance with an embodiment of the invention.
Figure 3:
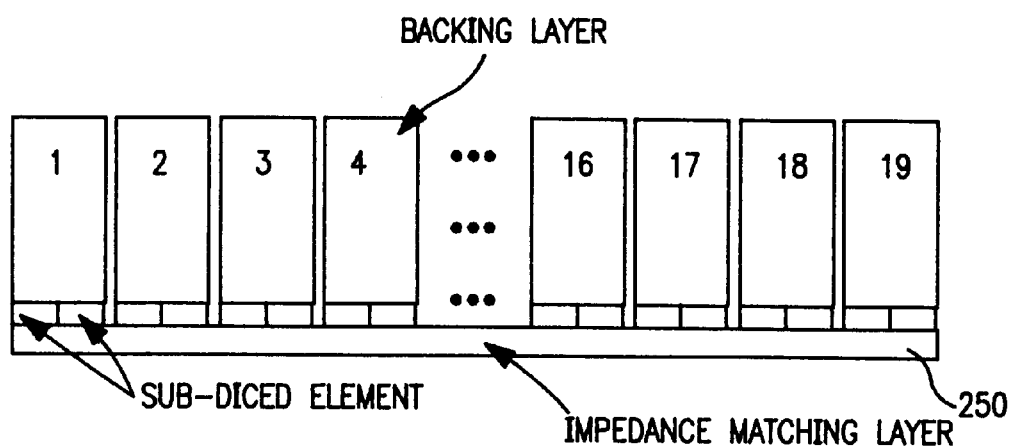
FIG. 3 is a cross-sectional view of the transducer array of the FIG. 2 embodiment.
Figure 4:
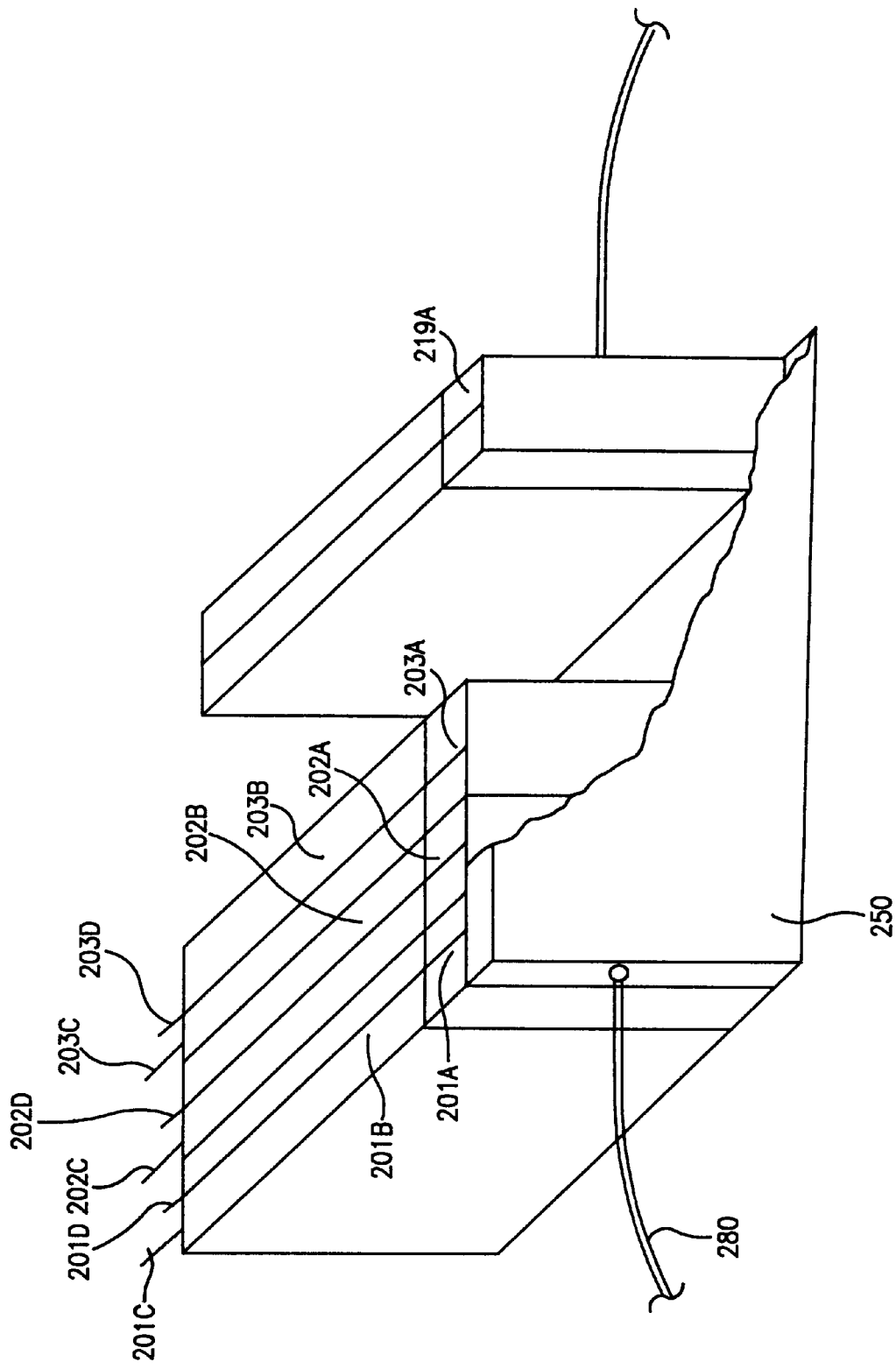
FIG. 4 is a perspective partially broken away view of the transducer array of the FIG. 2 embodiment.
Figure 5:
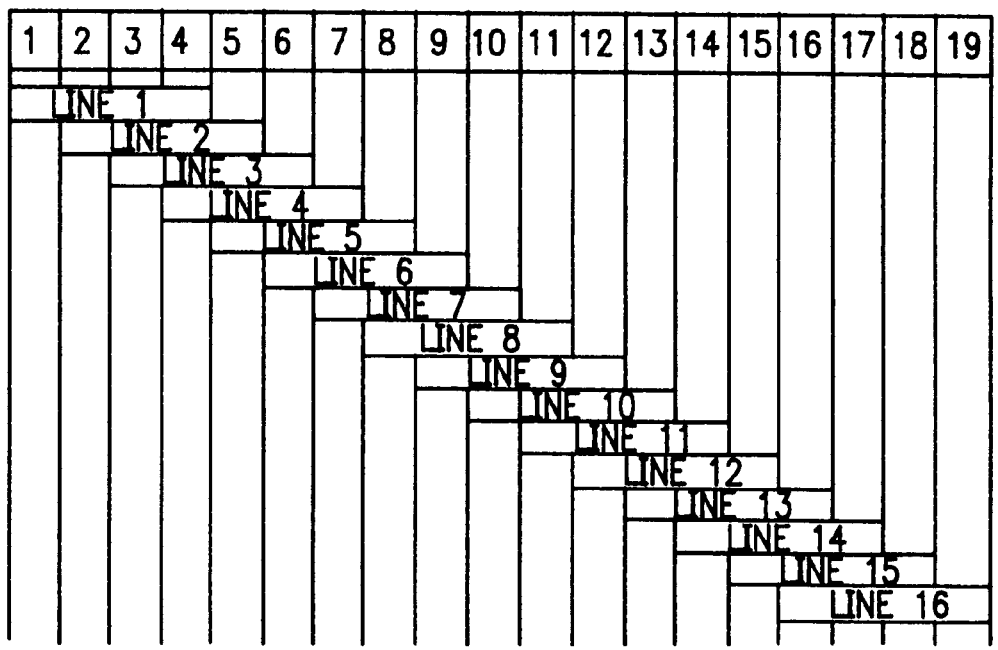
FIG. 5 illustrates a line sequence generated by a transducer array of an embodiment of the invention.

Referring to FIG. 2, there is shown a transducer array 100, which, in the present embodiment is a linear array, mounted on a head and secured with a rubber band 290. A two dimensional array could also be used. Reference can also be made to the diagrams of FIGS. 3 and 4. A flexible sheet or substrate 250 is used that can conform to the shape of the skull and provides acoustic impedance matching. In one working embodiment, a flexible plastic sheet having a thickness which is an integral number of quarter wavelengths was used. The elements of this array (see FIG. 4) were 19 rectangular piezo ceramic crystals 201A, 202A, 203A . . . 219A, although it will be understood that any suitable number of crystals can be utilized. The crystals are secured to the substrate 250 using an adhesive such as a conductive epoxy. Each crystal has a respective backing block, 201B, 202B, 203B . . . 219B, the backing blocks providing damping and also being secured with conductive epoxy. Respective signal wires 201C, 202C, 203C . . . 219C are coupled to one side of each crystal and respective ground wires 201D, 202D, 203D, . . . 219D, are coupled to the other side of each crystal. In an embodiment hereof, for a scanning resolution of 4 mm, the individual transducer has a square shape with side length of 13.4 mm and irradiates at a frequency of 1.85 MHz. [The preferred frequency range is 1.5 to 2.25 MHz, at which skull attenuation is minimized.] In order to provide 16 scanning lines spaced 4 mm apart, the piezo crystals are arranged in the illustrated segmental linear array. In this arrangement each transducer comprises four rectangular bars (3.4×13.4) mm each, and a scanning line is generated by firing four bars at a time. In this case 19 piezo ceramics can form 16 consecutive scanning lines. The line sequence is shown in FIG. 5, where the individual bars are numbered from 1 to 19. Penetration depth is in the range 15 to 20 cm and range resolution is about 1 mm.

The described segmented linear array of this embodiment has a disadvantage of well defined side lobes. The lobes usually result from width and length mode vibration of the excited crystal. Although their intensity is relatively low (−40 dB), they still can create artifacts in the image. For this reason each individual piezo ceramic bar is further sub-diced into two elements.

The movements of the surfaces of the transducer radiate energy into the medium which is adjacent to them, and it can be shown that the amount of penetrated and reflected energy depends upon the characteristic impedance of both media. Therefore, some of the irradiated energy reflects back into the transducer at each of its surfaces. If at this time, an instantaneous voltage with varying amplitude is applied to the transducer, a new wave is generated and the resultant wave in the transducer equals the superposition of the propagating and reflecting waves. If the thickness of the transducer is equal to one half of the wavelength at resonance, both waves reinforce each other and stable constructive interference occurs. At this point the vibration amplitude of the transducer surfaces is maximum, and the resultant ultrasonic wave has maximum energy. Since the irradiated wave has a frequency equal to the transducer's mechanical resonance, the transducer has maximum sensitivity if also used as a receiver.

For clinical diagnostic applications, in general, the transducer can be excited with a high voltage (about 400 V) pulse with duration of several hundred nanoseconds. The irradiated wave is not confined to a single frequency, and has a wide frequency spectrum. The transducer must be able to respond to this short pulse and for this reason the transducer should be damped. Thus, the energy transfer efficiency is reduced, but the transducer response becomes less frequency dependent. The damping significantly reduces the mechanical quality factor $Q_M$ which increases the transducer's bandwidth, i.e., the sensitivity has a wider frequency response. Thus, the equivalent axial resolution improves.

Damping is provided by the block of highly absorbent material (201B, 202B, etc.) attached to the rear surface of the piezo crystal. The ideal backing material should have an acoustic impedance as close as possible to that of the piezo crystal. For the APC crystal used in an embodiment hereof, an advantageous backing is tungsten powder suspended in epoxy. Among the commercially available chemical elements, Tungsten is the most dense material, and the mixture will have very high acoustic impedance.

Since the transducers will be used for brain imaging in an application hereof, in order to have good physical contact between the transducer and the head, along with nonrefractive beam propagation, each transducer element is backed independently. The thickness of the backing block in an embodiment hereof is 25 mm, which introduces additional attenuation for the ultrasonic wave propagated into the backing block. The front surfaces of the transducers are attached to the flexible substrate as previously described. Thus, the 19 element linear array can be curved to match the individual shape of the head.

The flexible substrate 250 plays an important role in the array performance. It is used as an impedance transformer between the high impedance crystal and the low impedance head skin layer. Without it a substantial portion of the irradiated beam would be reflected back to the transducer.

The acoustic impedance and the thickness of the matching layer should be optimized to give the best axial resolution. A thickness equal to an integer multiple of quarter wavelengths provides maximum reinforcement of the ultrasound wave. For a particular implementation, the matching layer was developed by several multilayers until the best performance was obtained.

For optimum performance each transducer in the array can be electrically and water isolated. When a casing (not shown) is used, an additional sound insulator, such as rubber cork, can be placed between the case of the array and the transducers, which minimizes the coupling of ultrasonic energy to and from the case. This reduces ringing of the case, which can result in artifacts.

Figure 6:
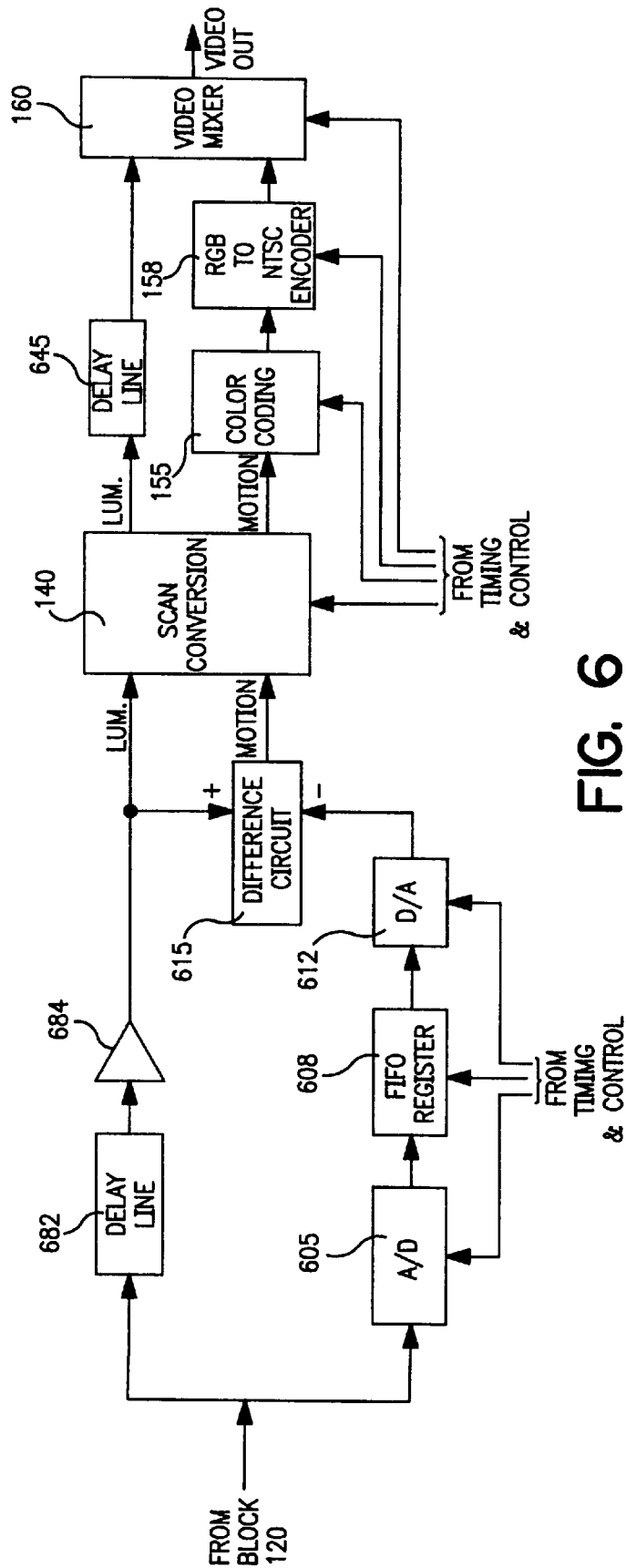
FIG. 6 is a block diagram that includes motion detection and display circuitry of the FIG. 1 embodiment.

FIG. 6 is a block diagram of the motion detection circuity and related circuitry represented by the blocks 130, 140, 150 and 160 of the FIG. 1 embodiment. The image signal from the block 120 is coupled to both an analog-to-digital converter 605 and to equalizing delay line 682. The output of analog-to-digital converter 605 is coupled to a first-in-first-out (FIFO) register 608, the output of which is coupled to a digital-to-analog converter 612 whose output is, in turn, an input to the negative input terminal of a difference circuit 615. The input to the positive terminal of the difference circuit 615 is the image signal delayed by the equalizing delay 682 and amplified by amplifier 684, this signal also being coupled as a luminance signal to digital scan converter 140. The scan converter 140, as well as the blocks 605, 608 and 612, all receive timing signals from the timing and control block 180 (FIG. 1). The difference signal is a motion signal because it represents the difference between frames, and therefore depends on motion in the image.

The scan converted motion signal is coupled to color coding circuit 155 which, in the present embodiment, produces color component signals R, G, B, which are, in turn, converted to an NTSC chrominance signal, which is one input to a video mixer 160. The other input to the video mixer 160 is the luminance signal output of converter circuit 140, after an equalizing delay (block 645). The output of video mixer 160 is the video that is coupled to display 170 and recorder 175 (FIG. 1).

In accordance with a feature hereof, the amplitude of motion is color coded using n levels of discrimination (where n can be any suitable number), n being 4 for an exemplary embodiment. If motion at a given location in the image is less than the lowest level of discrimination (the threshold), there will be no color at that location in the image. The threshold will preferably be set high enough to prevent noise from being displayed as color. As each discrimination level is reached, a different color is displayed.

Figure 7:
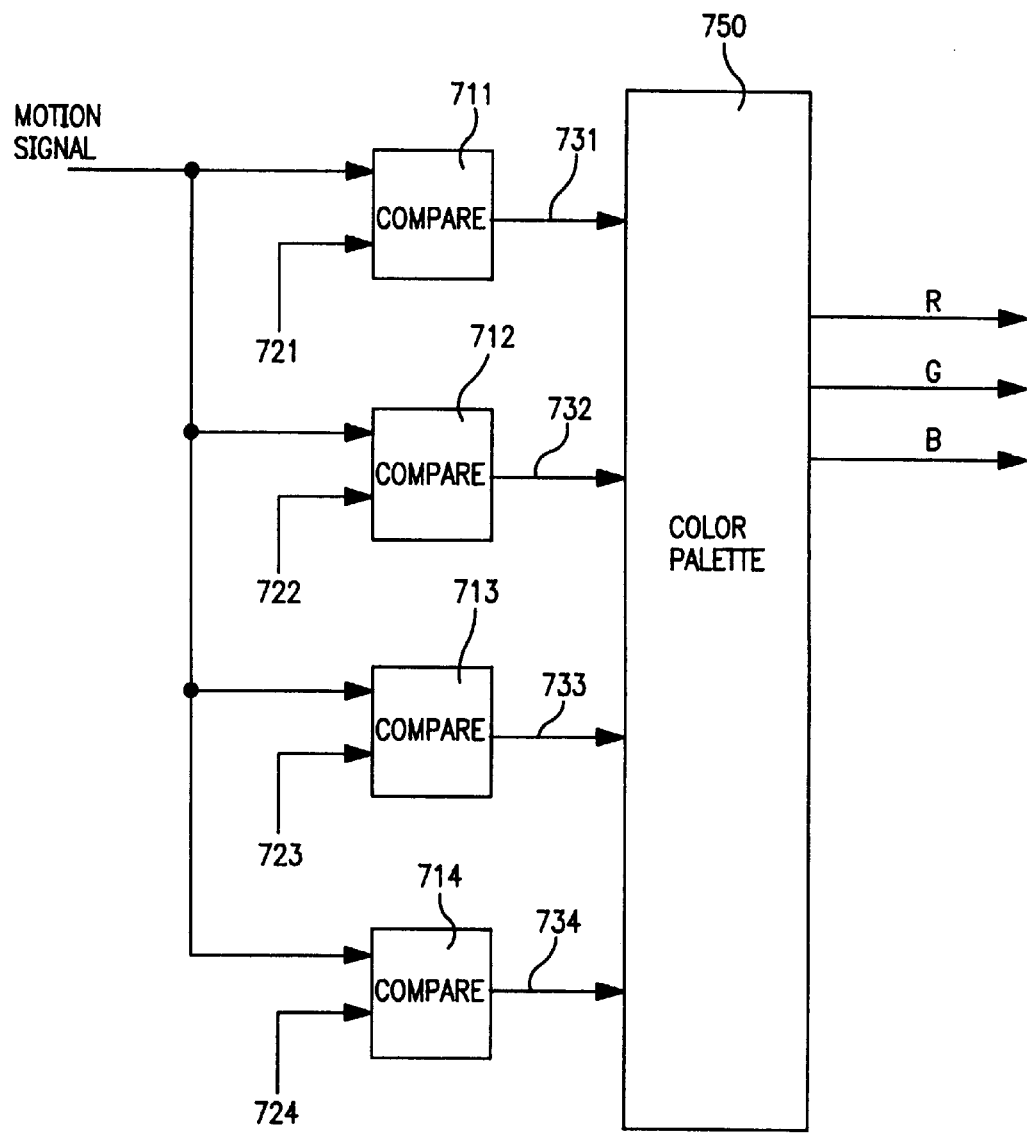
FIG. 7 is block diagram of a circuit for color coding of motion amplitude of the FIG. 6 embodiment.

FIG. 7 shows an embodiment of the color coding circuit 155 of FIG. 6. Four comparator circuits 711, 712, 713, and 714, are provided, and each has a different threshold level, determined by the potential applied at 721, 722, 723, and 724, respectively. Each comparator also receives the motion-representative signal from block 140. The comparator outputs are coupled to a color palette circuit 750, which may be implemented with a commercially available programmable color video chip. Accordingly, one of the four comparator outputs 731, 732, 733, or 734 will be input to the block 750 and will determine the output color composition. The color component signals, R, G, and B, are coupled to the NTSC encoding circuit 158 (FIG. 6) as previously described. In one embodiment hereof, the four discrimination levels were respectively coded (with increasing motion amplitude) as blue, green, yellow and red. Thus, in this example, absence of color in a given region indicates little or no motion in that region, blue indicates relatively small motion, and red indicates relatively large motion. The motion can be quantified with color to the extent desired.

The observed range pulsations are in the order of 0.01–0.2 mm, so the motion detection resolution should be in that range. Digital or analog subtraction could be used. In both methods digital frame storage is required to store the reference image, usually taken from the first scan. In the digital method the incoming image can be digitized, stored in a memory, and digitally subtracted from the existing reference (also stored in memory). The resultant data can be converted to an image using an analog to digital converter. The image shows only the places where interface motion accrues and signal amplitude is proportional to the motion amplitude. In order to achieve a resolution of 0.01 mm, the sampling frequency has to be around 160 MHz. It is, however, expensive to obtain a frame store with a capacity of 10 Mbytes for that frequency.

The illustrated embodiment uses analog subtraction. In this method, as described, the reference image is digitized and stored in memory. After that, the image is reconstructed and subtracted from the incoming analog signal. A mathematical model was developed to simulate the dual analog-digital-analog conversion, and to compare the reconstructed signal with the original one. The results from that model showed that if a sampling frequency of around 30 MHz and 10-bits resolution are used, the error between the original and reconstructed signals is less than 1%, which leads to a motion pickup resolution of less than 0.01 mm. Thus, by using this technique, commercially available components can be used, and the hardware can be clocked by the system clock, which is at 28.6363 MHz in this embodiment.

In the embodiment of FIGS. 1–6, the system is able to detect any interface motion within the 16 lines scanned area with a resolution of 0.01 mm. The incoming image formatted as 16 consecutive lines is processed in the indicated two parallel paths. The first one, the image is digitized by A/D converter operating at 10-bit 40 MHz and stored in the field memory-type FIFO 608. This image is used as a reference. In the second path, the incoming image is delayed about 50 ns (to compensate for the delay in the digital branch) and analogically subtracted from the reference image reconstructed by D/A converter 612 (10 bit, 40 MHz, in this embodiment). To minimize the subtraction error, the incoming and the reference images are temporally aligned by delay 682, which can be a multitab delay line.

If the reference image is not locked to any particular brain state, the direction of the motion loses its meaning. In such case, the difference circuit 615 can contain a full wave rectifier to flip the negative portion of the motion signal so that from this point on, the signal would be processed only based on the absolute value of its amplitude. However, if a "rest state" of the brain is established, this would not be necessary, as motion would be determined with respect to the rest state.

We claim:

1. A method for producing an image of a human brain in a skull that indicates location and magnitude of brain motion, comprising the steps of:

providing a transducer array that conforms to the skull;

coupling energizing signals to said transducer array to produce transmitted ultrasonic energy;

receiving reflected ultrasonic energy at said transducer and producing receiver signals;

storing receiver signals to obtain stored signals;

producing a motion signal as a function of the difference between said receiver signals and said stored signals; and displaying said motion signals.

2. The method as defined by claim 1, wherein said displaying step comprises quantifying the amplitude of motion represented by said motion signals to produce motion amplitude signals, and displaying said motion amplitude signals.

3. The method as defined by claim 2, wherein said displaying step comprises color coding said motion amplitude signals with different colors for different motion amplitudes, and displaying said color coded motion amplitude signals.

4. The method as defined by claim 2, further comprising displaying said receiver signals.

5. The method as defined by claim 4, wherein said motion signals and said receiver signals are displayed together.

6. The method as defined by claim 5, wherein said receiver signal is displayed as a luminance signal.

7. The method as defined by claim 1, further comprising displaying said receiver signals.

8. The method as defined by claim 7, wherein said motion signals and said receiver signals are displayed together.

9. The method as defined by claim 8, wherein said receiver signal is displayed as a luminance signal.

* * * * *